United States Patent [19]

Connor et al.

[11] E Re. 30,339

[45] Reissued Jul. 15, 1980

[54] **CONVERSION OF ACID S, PRODUCED BY THE ORGANISM *POLYANGIUM CELLULOSUM* VAR. *FULVUM* INTO ACID F**

[75] Inventors: David T. Connor, Ann Arbor, Mich.; Maximilian von Strandtmann, New Castle, Del.

[73] Assignee: Warner-Lambert Company, Morris Plains, N.J.

[21] Appl. No.: 924,469

[22] Filed: Jul. 14, 1978

Related U.S. Patent Documents

Reissue of:

[64] Patent No.: 4,076,940
Issued: Feb. 28, 1978
Appl. No.: 794,180
Filed: May 5, 1977

[51] Int. Cl.[2] ..... C09B 23/00

[52] U.S. Cl. ..... 542/430; 542/447; 424/115; 424/121; 424/122

[58] Field of Search ..... 542/430, 447; 424/115, 424/121, 122

[56] References Cited

U.S. PATENT DOCUMENTS

| | | | |
|---|---|---|---|
| 3,651,216 | 3/1972 | Ringel et al. | 424/115 |
| 3,804,948 | 4/1974 | Strandtmann et al. | 424/122 |
| 4,001,398 | 1/1977 | Connor et al. | 424/122 |
| 4,009,261 | 2/1977 | Connor et al. | 424/122 |
| 4,016,257 | 4/1977 | Connor et al. | 424/122 |

*Primary Examiner*—Paul F. Shaver
*Attorney, Agent, or Firm*—Walter Patton; Stephen Raines; Albert H. Graddis

[57] ABSTRACT

A process for the conversion of the major antifungal antibiotic, acid S (ATCC No. 25532) isolated from the fermentation of Polyangium cellulosum var. fulvum into the minor antibiotic, acid F, from the same fermentation is described wherein acid S is methylated with diazomethane to provide acid S methyl ester which is then oxidized with silver carbonate on celite to obtain the corresponding keto ester S, which is subsequently reduced with sodium borohydride to give a mixture of acid S methyl ester and acid F methyl ester. These esters are readily separated by preparative thin layer chromatography and the acid F methyl ester is hydrolyzed with sodium hydroxide solution to provide acid F.

3 Claims, No Drawings

CONVERSION OF ACID S, PRODUCED BY THE ORGANISM *POLYANGIUM CELLULOSUM* VAR. *FULVUM* INTO ACID F

Matter enclosed in heavy brackets [ ] appears in the original patent but forms no part of this reissue specification; matter printed in italics indicates the additions made by reissue.

The present invention is concerned with a process for the conversion of the major antifungal antibiotic (acid S) isolated from the fermentation of Polyangium cellulosum var. fulvum into the minor antibiotic (acid F) from the same fermentation. Acid F is isolated either in small amounts or in many cases not at all from the fermentation medium. Thus, in order to have an adequate supply of acid F, it has been found necessary to design a process for the conversion of the readily available acid S into acid F.

Acid S and acid F are described in U.S. Pat. Nos. 3,651,216 and 3,804,948. As disclosed in these patents, both acid S and acid F are potent antifungal agents. In addition, U.S. Pat. No. 3,804,948 describes the chemical preparation of the methyl ester of acid S. Keto ester S, a derivative of acid S, disclosed in U.S. Pat. No. 3,932,620 is also used in the process of this invention.

The process of the invention is shown in Scheme A as follows:

*SCHEME A*

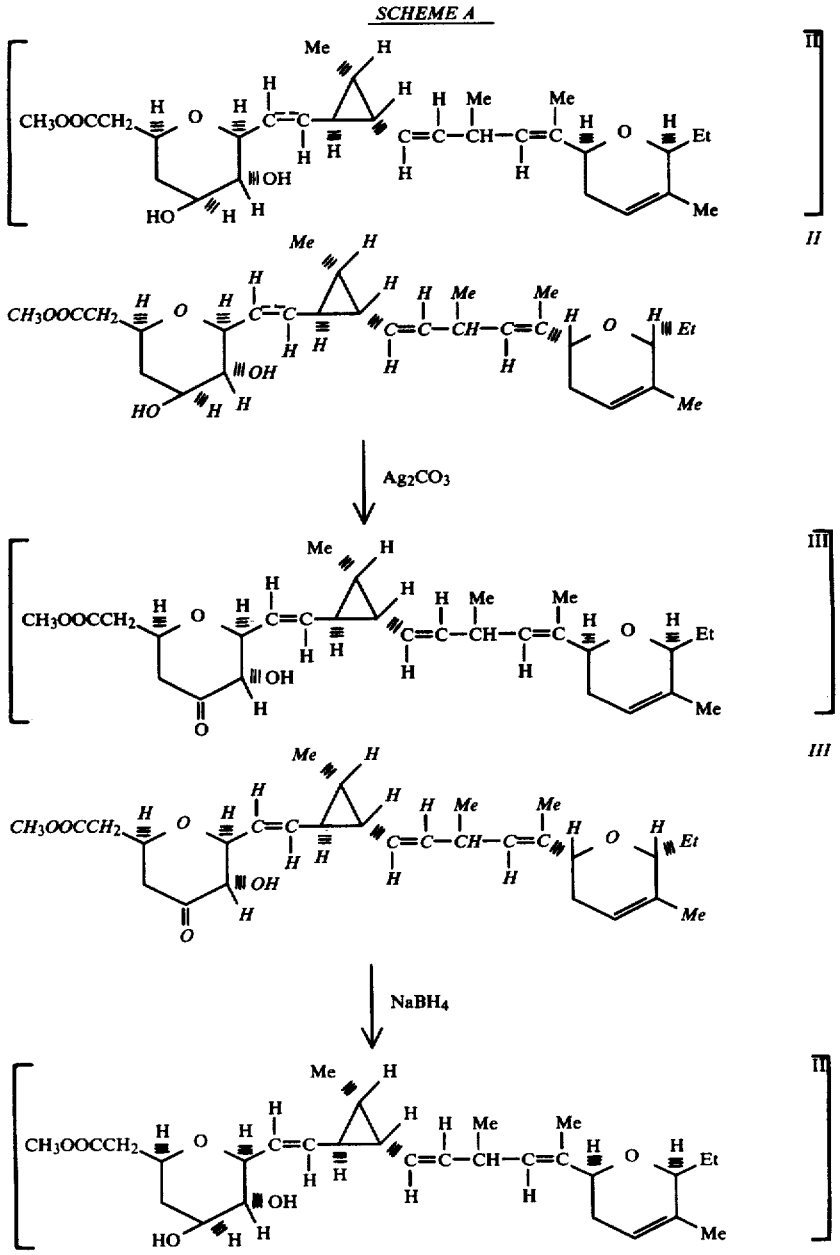

-continued
SCHEME A
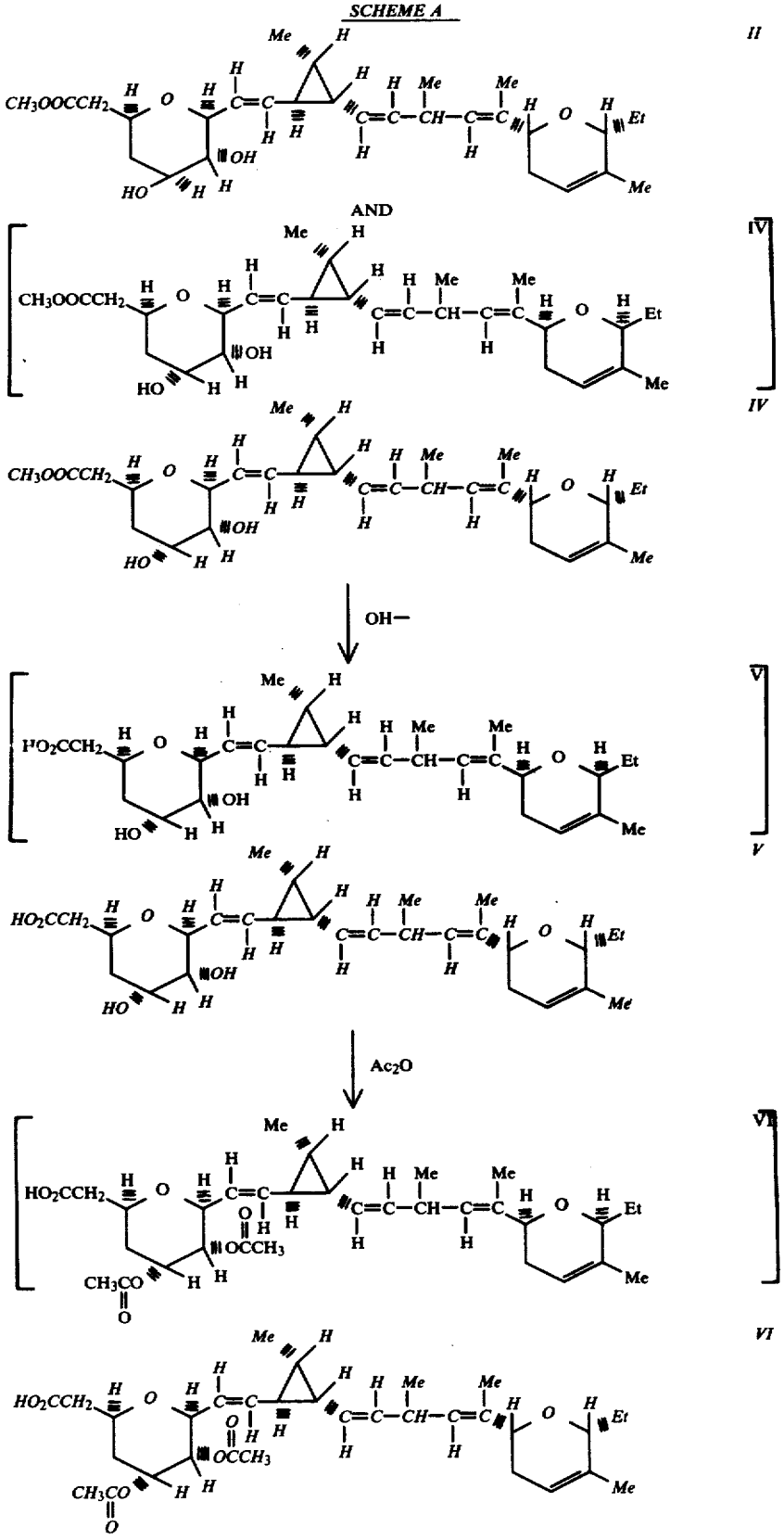
Acid S (I) is methylated with diazomethane to provide acid S methyl ester II, which is oxidized with silver carbonate on celite to obtain keto ester S (III). Attempts to oxidize acid S directly to keto S yields tars, but selective oxidation of acid S methyl ester to keto ester S, following the procedure described in U.S. Pat. No. 3,932,620 is successful.

Keto ester S(III), in an alcoholic solvent such as methanol, is reduced with an alkali metal borohydride, typically sodium borohydride, to provide a mixture of acid S methyl ester II and acid F methyl ester IV. The reduction step may be conducted under nitrogen. These esters are readily separated by preparative thin layer chromatography. A typical solvent system which may be used for this separation is ethyl acetate-cyclohexane in a ratio of 4:1. Variations of this solvent system, commonly used in thin layer chromatography separations are also suitable.

The acid F methyl ester IV thus obtained is hydrolyzed to obtain acid F (V). The hydrolysis is conducted in an alcoholic solvent, such as methanol, using alkali metal hydroxide, typically sodium hydroxide. The hydrolysis step may be conducted under nitrogen.

To confirm the structure of acid F (V), the diacetate VI of the semi-synthetic product was prepared. A sample of natural acid F (VII) obtained from the fermentation was also acetylated to obtain acid F diacetate VIII. The NMR spectra of the two diacetates VI and VIII were found to be identical in all respects, indicating that the semi-synthetic product VI is acid F diacetate. Thus, the semi-synthetic product V is identical to natural acid F (VII) isolated from the fermentation of Polyangium cellulosum var. fulvum. The infra-red spectra of semi-synthetic acid F (V) and natural acid F (VII) are also identical.

The following examples are provided to further illustrate the invention and are not be construed as limiting the scope of the invention.

EXAMPLE 1

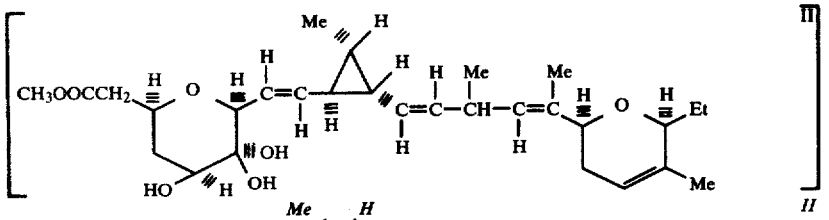

II

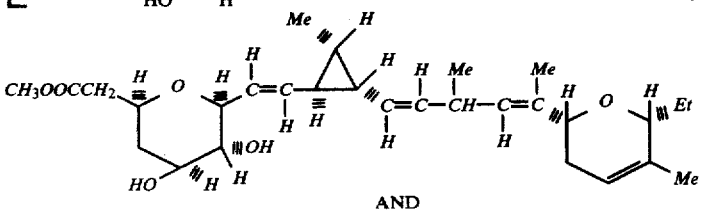

AND

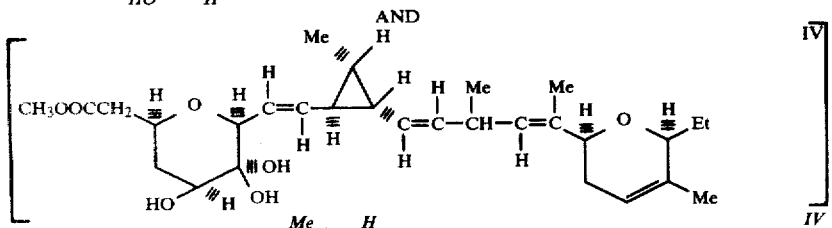

IV

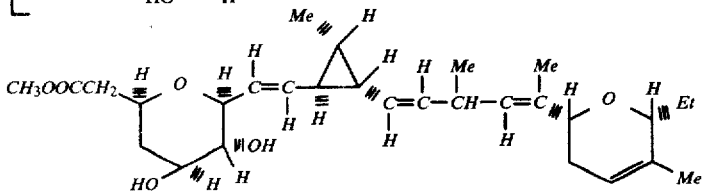

Acid S Methyl Ester and Acid F Methyl Ester

Sodium borohydride (230 mg, 0.00575) is added to a solution of keto ester S (230 mg, 0.00047 mole) in methanol (35 ml). The reaction mixture is stirred under nitrogen for 2 hours. The solvent is evaporated under reduced pressure to give a white gummy solid. The solid is dissolved in water, acidified with 1 N hydrochloric acid and extracted with chloroform. The extracts are dried over $MgSO_4$ and evaporated to give a pale yellow gum (187 mg). The gum is fractionated into two products by preparative TLC with the solvent system ethyl acetate-cyclohexane (4:1). Acid S Methyl Ester (most polar compound) is isolated as a colorless oil (86 mg., 37%), Acid F Methyl Ester (least polar compound) is isolated as a colorless oil (49 mg., 21%). Diagnostic TLC indicates both products to be homogeneous and both have the same Rf values as the corresponding esters derived from the natural acids.

EXAMPLE 2

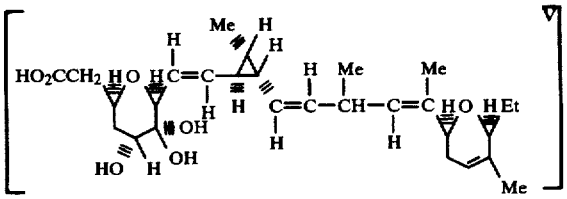

V

-continued

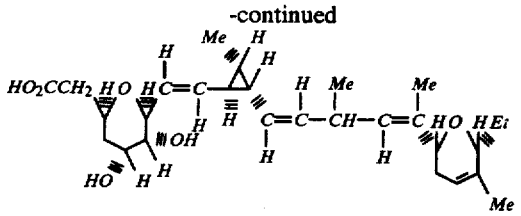

V

Acid F (Semi-synthetic)

1 N sodium hydroxide solution (3 ml) is added to a methanol solution of semi-synthetic acid F methyl ester (49 mg., 0.00001 mole). The reaction mixture is stirred at 90 under nitrogen for 30 minutes. The methanol is removed under pressure. The aqueous residue is acidified with 1 N hydrochloric acid and extracted with chloroform. The extracts are dried over magnesium sulfate and evaporated to give acid F as a colorless oil (25 mg., 53%).

IR $\gamma$ max broad 3600–3200 and 2800–2500 (OH), 1720 $cm^{-1}$(CO)

| *Mass Spectrum* | |
|---|---|
| *Observed molecular ion* | *474.3010* |
| *Calculated for $C_{28}H_{42}O_5$* | *474.2981* |

m/e (relative intensity) 474(14), 456(9), 445(29), 379(19), 361(8), 279(64), 245(19), 235(21), 195(75) and 193(100).

EXAMPLE 3

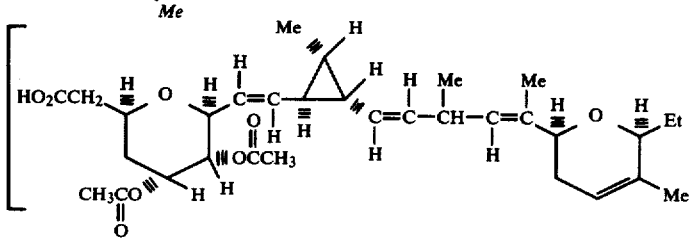

VI

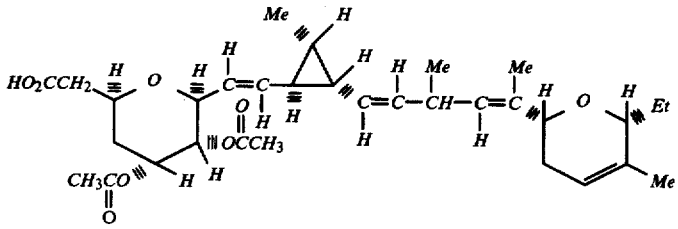

VI

Acid F Diacetate (Semi-synthetic)

Acetic anhydride (1 ml) is added to a solution of semi-synthetic acid F (25 mg) in pyridine (2 ml). The solution is allowed to stand at room temperature overnight, diluted with water, and evaporated to give acid F diacetate as a pale yellow gum (28 mg 90%).

IR $\gamma$ max broad 3500–3100 and 2800–2400(OH), 1745 (CO) and 1720 $cm^{-1}$(CO)

| *Mass Spectrum* | |
|---|---|
| *Observed molecular ion* | *558.3295* |
| *Calculated for $C_{32}H_{46}O_8$* | *558.3271* |

m/e (relative intensity) 558(17), 529(50), 463(21), 343(10), 305(10), 259(7), 245(23), 195(23) and 193(100).

NMR ($CDCl_3$) $\delta$ 0.89 (s, 3H, $CH_3$), 1.05 (m, 6H, $2CH_3$), 1.59 (s, 3H, $CH_3$), 1.64 (s, 3H, $CH_3$), 1.98 (s, 3H, $CH_3CO$), 2.14 (s, 3H, $CH_3CO$), 2.44 (q, 1H, $CH_2CO$), 2.65 (q, 1H, $CH_2CO$), 3.07 (m, 1H, bisallyl), 3.86 (q, 1H, CH—O), 4.07–4.29 (m, 3H, 3CH—O), 4.67 (q, 1H, CH—OAc), 5.06 (q, 1H, vinyl), 5.25 (d, 1H, vinyl), 5.32–5.52 (m, 4H, 3 vinyl and 1 CH—OAc) and 5.57 (d, 1H, vinyl).

EXAMPLE 4

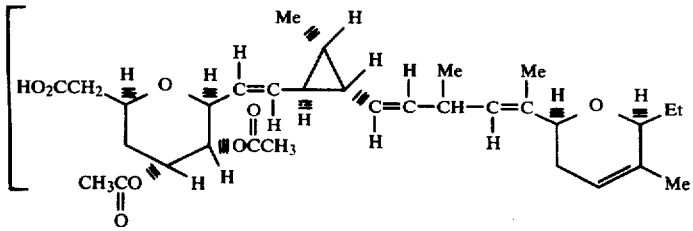

VIII

-continued

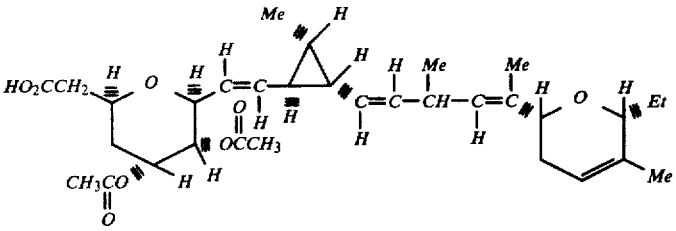

VIII

Acid F Diacetate (From natural product)

Acetic anhydride (1 ml) is added to a solution of acid F (100 mg) in pyridine (2 ml). The solution is allowed to stand at room temperature overnight, diluted with water, and evaporated to give acid F diacetate as a light brown gum.

IR $\gamma$ max broad 3500–3100 and 2800–2400(OH), 1745(CO) and 1720 $cm^{-1}$(CO).

| *Mass Spectrum* | |
|---|---|
| *Observed molecular ion* | *558.3249* |
| *Calculated for* $C_{32}H_{46}O_8$ | *558.3271* |

m/e (relative intensity) 558(26), 529(44), 463(30), 343(12), 305(14), 259(14), 245(21), 195(90) and 193(100)

NMR ($CDCl_3$) $\delta$ 0.89 (s, 3H, $CH_3$), 1.05 (m, 6H, $2CH_3$), 1.59 (s, 3H, $CH_3$), 1.64 (s, 3H, $CH_3$), 1.98 (s, 3H, $CH_3CO$), 2.14 (s, 3H, $CH_3CO$), 2.44 (q, 1H, $CH_2CO$), 2.65 (q, 1H, $CH_2CO$), 3.07 (m, 1H, bisallyl), 3.86 (q, 1H, CH—O), 4.07–4.29 (m, 3H, 3CH—O), 4.67 (q, 1H, CH—OAc), 5.06 (q, 1H, vinyl), 5.25 (d, 1H, vinyl), 5.32–5.52 (m, 4H, 3 vinyl and 1CH—OAc) and 5.57 (d, 1H, vinyl).

We claim:

1. A process for preparing the substance acid F (V) having the following formula:

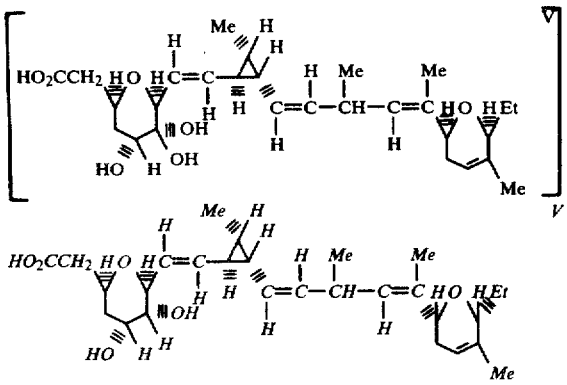

V which comprises the following steps:

A. Reducing an alcoholic solution of keto ester S (III) wherein the keto ester S has the following formula:

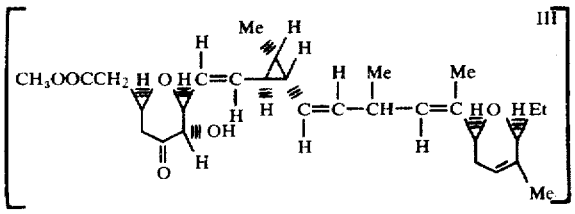

III

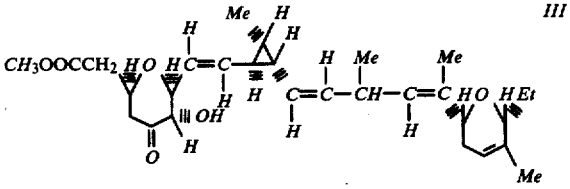

III with an alkali metal borohydride to obtain a mixture of acid S methyl ester II and acid F methyl ester IV having the following formulas:

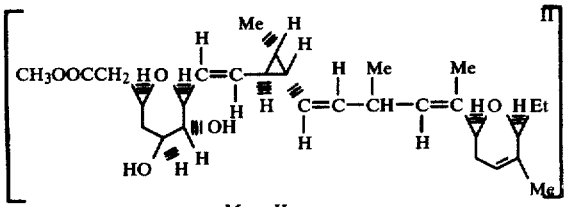

II

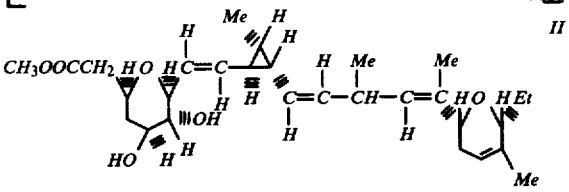

II

AND

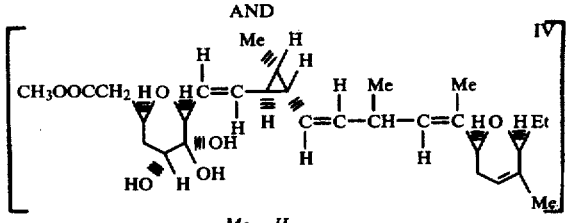

IV

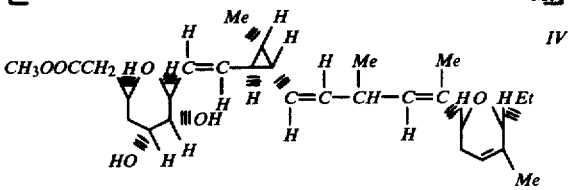

IV

B. Separating acid S methyl ester II and acid F methyl ester IV by preparative thin layer chromatography;

C. Hydrolyzing acid F methyl ester IV to obtain the desired acid F (V).

2. A process according to claim 1 wherein in Step A, the reduction is conducted in methanol using sodium borohydride.

3. A process according to claim 1 wherein in Step C, the hydrolysis is conducted in methanol using sodium hydroxide.

* * * * *